United States Patent [19]

Krivak et al.

[11] Patent Number: 4,717,561

[45] Date of Patent: Jan. 5, 1988

[54] PRECIPITATED SILICA CARRIER FOR VITAMINS

[75] Inventors: Thomas G. Krivak, Akron, Ohio; Stanley A. Heimburger, Pittsburgh, Pa.; James T. Dew, Sulphur, La.

[73] Assignee: PPG Industries, Inc., Pittsburgh, Pa.

[21] Appl. No.: 893,526

[22] Filed: Aug. 6, 1986

Related U.S. Application Data

[62] Division of Ser. No. 725,444, Apr. 22, 1985, Pat. No. 4,617,294.

[51] Int. Cl.$^4$ ............................................. C01B 33/12
[52] U.S. Cl. ..................................... 425/335; 423/331
[58] Field of Search ....................... 423/335, 338, 339

[56] References Cited

U.S. PATENT DOCUMENTS 2,942,830  8/1985  Thornhill ........................... 423/339
4,603,143  7/1986  Schmidt ............................. 514/458
4,617,294 10/1986  Krivak et al. ......................... 514/52

OTHER PUBLICATIONS

Chemical Engineers' Handbook, 3rd Edition, 1950, p. 963.

Primary Examiner—Gregory A. Heller
Assistant Examiner—Lori S. Freeman
Attorney, Agent, or Firm—Irwin M. Stein

[57] ABSTRACT

Free flowing, substantially dust-free, dense granular amorphous precipitated silica having a principal particle size of between about 0.14 millimeters and about 0.84 millimeters are described. This material is particularly suitable as an inert carrier for water-soluble and fat soluble nutritional supplements, e.g., vitamins, which are added to feeds for livestock.

6 Claims, No Drawings

PRECIPITATED SILICA CARRIER FOR VITAMINS

This is a division of application Ser. No. 725,444, filed Apr. 22, 1985 now U.S. Pat. No. 4,617,294.

DESCRIPTION OF THE INVENTION

Plant and animal products available for consumption by livestock vary in composition and nutritional value. Whole or ground cereals form a substantial portion of the rations of animals or birds. In general, the cereals and their by-products are very palatable to livestock. The cereals as a class of feed represent a high concentration of energy, but the cereals as individual grains are often lacking in both quantity and quality of protein or in the proper proportion of the so-called essential amino acids. Cereal by-products often have a high protein concentration, but are usually deficient in the quality of protein needed for optimum performance when fed as the only supplementary source to poultry and swine. In addition to the cereals and their by-products, oil-bearing seeds and their by-products, e.g., cottonseed, linseed, peanut products and soybean; forages, e.g., alfalfa, and their by-products; animal by-products, e.g., blood meal, bone meal, liver meal, and marine products, e.g., fish meal, are other examples of plant and animal products available for livestock consumption.

Some nutrients are required in larger amounts for some animals or birds than for others. Choline, for instance, has been shown to be required in relatively larger amounts in chick and poultry rations. Some feeds suitable in most respects for poultry or other animals may or may not be good sources of choline and other known nutritional substances and these may be added if the total ration lacks the amount required to adequately nourish the animal or bird. In recent years, vitamin $B_{12}$ has been found to have great value when added to certain feeds or combinations of feeds. It is now routinely added by most feed manufacturers in preparing certain feeds to insure the presence of enough of the substance for optimum growth. Thus, feed manufacturers and/or the feed compounders typically take care to provide in their feed products the minimum required amounts of essential nutrients and vitamins to insure adequate growth of the animal or bird ingesting the feed and to avoid the ill effects associated with the lack of an adequate amount of such nutrients and vitamins.

Certain vitamins, depending on their form, are absorbed onto inert carriers, e.g., finely-divided silica, and the resulting absorbate product admixed or blended with the feed. The carrier must be chemically inert with respect to the vitamin with which it is mixed and also harmless to the animal or bird which ingests the absorbate product. Further, the carrier must yield the absorbed vitamin to the livestock as it passes through the digestive tract, i.e., the vitamin must be available for use by the livestock.

It has now been discovered that certain amorphous precipitated silica is particularly suitable as an inert carrier for vitamins fed to livestock as a nutritional supplement. Such precipitated silica is a free-flowing, substantially dust free, granular material having a density of at least about 14 pounds per cubic foot, (224 kg/m³) a principal particle size of between about 0.14 millimeters and about 0.84 millimeters, a surface area of from about 140 to about 160 square meters per gram and an oil absorption of from about 160 to about 220 milliliters. More particularly, the aforesaid amorphous precipitated silica will have a density of between about 14 and 18 pounds per cubic foot, (224-288 kg/m³) preferably between about 15 and about 17 pounds per cubic foot (240-272 kg/m³).

Amorphous precipitated silica used as an inert carrier for vitamins in accordance with the present invention is free flowing and substantially dust-free. By substantially dust-free is meant that the silica contains less than 4, preferably less than 1, weight percent of material less than 200 Tyler mesh. A 200 Tyler mesh screen has an opening of 0.074 millimeters. Preferably, less than 5 weight percent of the silica will be less than 100 Tyler mesh. A 100 Tyler mesh screen has an opening of 0.147 millimeters. The particles of the silica will principally range between about 0.84 millimeters (sub 20 Tyler mesh) and 0.14 millimeters (plus 100 Tyler mesh). Typically less than 1 weight percent of the silica is greater than 0.84 millimeters (plus 20 Tyler mesh). Hence, at least about 94 weight percent of the particles are within the aforesaid range. The distribution of the particles within the aforesaid range is not critical. However, the products typically will have about 50 percent of the particles between −20 Tyler mesh and +60 Tyler mesh (0.25 millimeters) with the remainder between about −60 Tyler mesh and +100 Tyler mesh.

The surface area of the amorphous precipitated silica is a BET surface area, which is determined by the method of Brunauer, Emmett and Teller, J. Am. Chem. Soc., 60, 309 (1938). This method measures the absolute surface area of the silica by measuring the amount of gas adsorbed under special conditions of low temperature and pressure. Oil absorption of the silica is the volume in milliliters of dibutylphthalate oil necessary to wet 100 grams of the pigment. Oil absorption can be obtained using a method like the method described in ASTM D2414-65. The flowability of a solid may be measured using ASTM Method D1895.

The above-described amorphous precipitated silica is a white, granular, fine bead-like powder that is dry to touch. Despite appearing dry, the silica normally contains water, e.g., between about 2 and 8 percent "free water" by weight. Free water is that water which is removed from the silica by heating it at 105° C. for 24 hours. The silica also contains "bound water", which refers to that water removed by heating the silica at ignition temperature, i.e., 1000° C. for an extended period, e.g., 24 hours. Bound water can constitute between about 2 and 6 percent of the silica. Chemically, the finely-divided, granular amorphous precipitated hydrated silica contains at least 87, preferably at least 90 and more preferably 93 to 97 weight percent $SiO_2$ on an anhydrous basis, i.e., not including free-water.

The amorphous precipitated silica described above can be prepared by reaction of an aqueous solution of a soluble silicate, e.g., sodium, lithium or potassium silicate, most usually sodium silicate, with inorganic mineral acid, most notably carbonic acid, sulfuric acid or hydrochloric acid. Typically, sodium silicate having an $Na_2O:SiO_2$ ratio of about 3.3 is used to prepare the aqueous solution of the soluble silicate. Particularly suited as the mineral acid is carbonic acid, which is formed in situ by the introduction of carbon dioxide into the silicate solution. This method for preparing amorphous, precipitated silica is described in U.S. Pat. No. 2,940,830. The resulting precipitated silica is usually washed in suitable vessels to remove a portion of the soluble alkali metal inorganic salt incorporated therein during the precipitation process and thereafter the pH of the silica adjusted with an inorganic mineral acid, usually hydrochloric acid (although sulfuric acid may be used), to a final essentially neutral pH of between about 6.5 and about 7.3. The resulting silica is dried in a rotary or drum dryer and the dried product classified, e.g., by screening, to obtain the principal particle size distribution described hereinabove. Preferably, the dried silica is conveyed with agitation, e.g., pneumatically, to the classification step. Agitation of the finely-divided silica assists in the formation of the bead-like, essentially spherical particles. Agitation followed by classification also reduces a potential source of −200 Tyler mesh silica product produced by abrasion of the silica particles as a result of handling of the dry product—such fines being produced and then screened away from the final product. Hence, the silica product of the present invention is essentially non-friable (non-brittle) and is sufficiently hard so that it resists further degradation during further handling and processing, e.g., during blending with the vitamin(s) and feed and during storage and transportation.

Vitamins absorbed by the amorphous precipitated silica of the present invention may be any of those fat soluble or water soluble vitamins which are nutritionally essential to livestock. A suggested definition for vitamins is, "an organic substance of nutritional nature which in low concentrations, as an intrinsic part of enzyme systems, catalyzes reactions required by the organism, and the organism may or may not have a capacity for the biosynthesis of the substance." As used herein, the term vitamin is intended to include vitamers, which are organic compounds structurally related to the particular vitamin which possess similar activity. Further, the term vitamin and/or vitamer is intended to include the pure compound, isomers thereof and derivatives, e.g., esters, which are utilized as the market form or source of the vitamin.

Fat-soluble vitamins are vitamins A, D, E, and K while the water-soluble vitamins are vitamins C and the B group vitamins. Such and other vitamins may be absorbed onto the silica as such, provided the vitamin is a liquid at the temperatures of use, or the vitamin may be incorporated with the silica in the form of an aqueous dispersion or an oil concentrate. Typically, the vitamin, e.g., vitamins A, D and E, is incorporated into an oil and used as an oil concentrate.

Among the vitamins that may be utilized in accordance with the present invention are vitamin A, vitamin D, vitamin E (alpha-tocopherol), vitamin $B_1$ (thiamine), vitamin $B_2$ (riboflavin), niacin, vitamin $B_6$ (pyridoxine), biotin, pantothenic acid, vitamin $B_{12}$ choline, vitamin C (ascorbic acid), folic acid, para-aminobenzoic acid, and inositol.

The amount of vitamin mixed with the silica will vary depending on the end use of the vitamin supplement. As indicated, the needs of various livestock, i.e., animals or poultry, for the various essential vitamins varies and depends, in part, on the presence or absence of such vitamins in the feed given to the livestock. Further, a silica absorbate containing relatively small amounts of vitamin may be used with the feed or silica containing relatively larger amounts of vitamin may be added to the feed as a concentrate. Consequently, the silica may contain between about 0.02 and about 50 weight percent of at least one vitamin, which absorbate is used as a vitamin supplement. The amount of vitamin added to the silica will be such as to provide a nutritionally effective amount of the vitamin or vitamins absorbed thereon to the livestock, i.e., an amount needed to adequately nourish the livestock. The vitamin and/or its source, e.g., liquid concentrate, and the silica may be blended or mixed by any conventional liquid-solid equipment means useful for admixing materials of the physical characteristics of the silica and vitamin used herein.

The present invention is more particularly described in the following example which is intended as indicative of the bioavailability of vitamins when used with the silica of the present invention.

EXAMPLE 1

Selenium-deficient, vitamin E-depleted chicks were used to test the vitamin E biopotency of four dry preparations of vitamin E compared to a standard. The animal used in the evaluation shows reduced growth, impaired efficiency of feed utilization and the disease exudative diathesis unless fed adequate amounts of vitamin E or selenium. Use of a low selenium, tocopherol-free semipurified basal diet supplemented with graded levels of each of the vitamin E preparations results in incremental improvements in growth and feed utilization and in reduced incidence of exudative diathesis. This reduced instance of exudative diathesis, most specific for available vitamin E in the diet, was used to evaluate biopotency.

Day-old male vitamin E- and selenium-depleted single comb white leg horn chicks were used for the evaluation. The chicks were housed in thermostatically controlled battery brooders equipped with raised wire floors. Feed and water were provided ad libitum. The chicks were fed a low selenium (less than 0.02 parts per million), tocopherol-free semipurified diet containing adequate amounts of all other known nutrients. The diet was supplemented with graded levels of a vitamin E (0, 5, 10, 20, 40, or 80 IU/kg) from each of the sources tabulated in Table 1.

TABLE 1

| Source | Potency | Experimental Code |
|---|---|---|
| Vitamin E[1], USP | 976 IU/gm | STD |
| Experimental Silica[2] + Vitamin E | 510 IU/gm | A |
| Flo-Gard ® Type Silica[3] + | 502 IU/gm | B |

TABLE 1-continued

| Source | Potency | Experimental Code |
|---|---|---|
| Vitamin E | | |
| Hi-Sil ® EP Silica[4] + Vitamin E | 521 IU/gm | C |
| Zeosyl 110 SD[5] + Vitamin E | 517 IU/gm | D |

[1]Di-alpha-tocopheryl acetate.
[2]Silica product of the present invention.
[3]An amorphous precipitated spray dried silica having a surface area of about 150 m$^2$/g, an oil absorption of about 290 ml, a bulk density of about 12 lbs/ft$^3$ (192 kg/m$^3$) and a median particle size (as measured by Coulter Counter) of about 70 microns.
[4]An amorphous precipitated silica having a surface area of about 60 m$^2$/g, an oil absorption of about 175 ml, a bulk density of about 14 lbs/ft$^3$ (224 kg/m$^3$) and a median particle size (as measured by Coulter Counter) of about 9 microns.
[5]A finely granulated type of hydrated silicon dioxide having a reported surface area of about 120-150 m$^2$/g, reported oil absorption of about 180-200 cc/100 g (Linseed Oil Rub-Out Method) a bulk density of 13-15 lb/ft$^3$, (208-240 kg/m$^3$) and a reported average particle size of 12-14 microns.

The chicks were reared to two weeks of age. Gain in body weight, mortality, efficiency of feed utilization and incidence of exudative diathesis were recorded for each triplicate lots of ten chicks each per treatment. Results are presented in Tables 2-4.

Each test preparation of vitamin E increased the rate of growth, reduced the ratio of feed to gain, reduced mortality and reduced the incidence of exudative diathesis. The overall results, as ranked by overall means for each performance perameter by source of vitamin E, indicated that preparations A-D sustained growth with efficacies comparable to the standard. The various preparations differed with respect to efficacy in prevention of exudative diathesis (Table 4). When these data were fitted for each vitamin E preparation to log dose-probit of response models, the efficacies could be expressed as the effective dietary concentration to prevent exudative diathesis in 50 percent of the population ($EC_{50}$) (Table 6). The data suggested that preparations A and B had the greatest biopotencies of any of the dry forms tested. Preparation A was as efficacious as the Standard (Table 6). The data for preparations B, C, and D overlapped the data for the Standard and for a preparation (not reported) used in the study (ranked "B") that was significantly below the standard statistically.

TABLE 2

Influences of Vitamin E Preparations on Two-Week Gain of Chicks.

| Source | level, IU/kg | | | | | |
|---|---|---|---|---|---|---|
| | 0 | 5 | 10 | 20 | 40 | 80 |
| Std. | 29.5 ± 1.5 | 44.7 ± 1.3 | 45.3 ± 0.6 | 59.0 ± 3.0 | 55.3 ± 3.2 | 57.2 ± 3.2 |
| A | — | 35.9 ± 2.6 | 43.4 ± 4.7 | 44.7 ± 4.6 | 58.0 ± 1.6 | 52.2 ± 3.0 |
| B | — | 42.7 ± 1.6 | 45.8 ± 1.2 | 47.1 ± 2.4 | 52.5 ± 4.1 | 59.0 ± 2.0 |
| C | — | 37.2 ± 1.8 | 40.1 ± 1.2 | 42.1 ± 2.2 | 53.4 ± 6.6 | 58.1 ± 5.0 |
| D | — | 33.2 ± 3.1 | 40.1 ± 6.4 | 45.5 ± 3.8 | 49.1 ± 3.0 | 55.9 ± 0.8 |

TABLE 3

Influence of Vitamin E Preparation on Efficiency of Feed Utilization (feed/gain)

| Source | level, IU/kg | | | | | |
|---|---|---|---|---|---|---|
| | 0 | 5 | 10 | 20 | 40 | 80 |
| Std. | 2.65 ± .10 | 2.45 ± .26 | 2.10 ± .07 | 1.93 ± .05 | 2.08 ± .07 | 2.08 ± .06 |
| A | — | 2.44 ± .11 | 2.27 ± .06 | 2.22 ± .10 | 1.94 ± .08 | 2.18 ± .03 |
| B | — | 2.10 ± .12 | 2.09 ± .06 | 2.24 ± .04 | 2.19 ± .15 | 2.06 ± .05 |
| C | — | 2.26 ± .10 | 2.28 ± .04 | 2.31 ± .11 | 2.09 ± .08 | 2.00 ± .04 |
| D | — | 2.56 ± .12 | 2.35 ± .24 | 2.19 ± .13 | 2.21 ± .06 | 2.08 ± .02 |

TABLE 4

Influence of Vitamin E Preparation on the Incidence (%) of Exudative Diathesis

| Source | level, IU/kg | | | | | |
|---|---|---|---|---|---|---|
| | 0 | 5 | 10 | 20 | 40 | 80 |
| Std. | 100.0 ± 0.0 | 80.0 ± 5.8 | 76.7 ± 6.7 | 43.3 ± 6.7 | 33.3 ± 12.0 | 16.7 ± 3.3 |
| A | — | 90.0 ± 0.0 | 73.3 ± 8.8 | 53.3 ± 6.7 | 36.7 ± 3.3 | 16.7 ± 6.7 |
| B | — | 76.7 ± 13.3 | 70.0 ± 5.8 | 46.7 ± 12.8 | 46.7 ± 3.3 | 6.7 ± 6.7 |
| C | — | 96.7 ± 3.3 | 83.3 ± 3.3 | 70.0 ± 10.0 | 63.3 ± 18.6 | 23.3 ± 3.3 |
| D | — | 96.7 ± 3.3 | 83.3 ± 3.3 | 63.3 ± 3.3 | 53.3 ± 3.3 | 23.3 ± 6.7 |

TABLE 5

Overall Averages for Each Source of Vitamin E

| Source | Gain g | Feed/gain | Exudative Diathesis % |
|---|---|---|---|
| Std | 48.0$^{a,1,2}$ | 3.27[1] | 59.8[1] |
| A | 43.9$^{ab}$ | 2.29 | 61.7 |
| B | 46.1$^a$ | 2.22 | 57.8 |
| C | 43.9$^{ab}$ | 2.25 | 72.8 |
| D | 42.8$^{ab}$ | 2.32 | 70.0 |

[1]Mean ± SE for 18 lots of 10 chicks each per treatment.
[2]Means with like superscripts are not significantly different (P > .05).

TABLE 6

Comparison of Relative Efficacies of Vitamin E Preparations in Preventing Exudative Diathesis in the Chick

| Preparation | $EC_{50}^{1}$ IU/kg | 95% Confidence Limits | RANK |
|---|---|---|---|
| Std | 20.0 | 13.1–30.6 | A |
| A | 23.7 | 21.6–26.0 | A |
| B | 19.2 | 4.8–73.9 | AB |
| C | 41.5 | 26.0–96.6 | AB |
| D | 35.7 | 26.4–53.1 | AB |

[1]Level required to protect 50% of the population from exudative diathesis, expressed in terms of International units as originally indicated for each preparation. $EC_{50}$ values were computed from the individual regressions for each vitamin E source using log-probit of response model.

While the invention has been described in detail with respect to certain embodiments thereof, it is understood that the invention is not intended to be limited to such details except as and insofar as they appear in the appended claims.

We claim:

1. A substantially dust-free, granular amorphous precipitated silica having a density of at least 14 pounds per cubic foot, wherein at least 94 percent of the silica particles are within the range from 0.14 millimeters to 0.84 millimeters, a BET surface area of from about 140 to 160 square meters per gram and an dibutylphthalate oil absorption of from about 160 to 220 milliliters per 100 grams.

2. The precipitated silica of claim 1 wherein the bulk density is from about 14 to about 18 pounds per cubic foot.

3. The precipitated silica of claim 1 wherein the bulk density is from about 15 to 17 pounds per cubic foot.

4. A substantially dust-free, granular amorphous precipitated silica having a density of from about 14 to about 18 pounds per cubic foot, a BET surface area of from about 140 to 160 square meters per gram, an dibutylphthalate oil absorption of from about 160 to 220 milliliters per 100 grams, and a particle size distribution wherein at least 94 percent of the silica particles are within the size range of from about 0.14 millimeters to about 0.84 millimeters.

5. The precipitated silica of claim 4 wherein the bulk density is from about 15 to 17 pounds per cubic foot.

6. The precipitated silica of claim 4 wherein about 50 weight percent of the particles are between 0.84 millimeters and 0.25 millimeters and the remainder are between about 0.25 millimeters and about 0.14 millimeters.

* * * * *

UNITED STATES PATENT AND TRADEMARK OFFICE
CERTIFICATE OF CORRECTION

PATENT NO. : 4,717,561

DATED : January 5, 1988

INVENTOR(S) : Thomas G. Krivak et al

It is certified that error appears in the above-identified patent and that said Letters Patent is hereby corrected as shown below:

Cover page, Second Column, Line 5,

"2,942,830   8/1985 Thornhill.....423/339" should be
--2,940,830   6/1960 Thornhill.....423/339--.

Signed and Sealed this

Fourth Day of October, 1988

Attest:

DONALD J. QUIGG

*Attesting Officer*    *Commissioner of Patents and Trademarks*